(12) United States Patent
Clancy et al.

(10) Patent No.: US 10,888,353 B2
(45) Date of Patent: *Jan. 12, 2021

(54) EXPANDABLE ACCESS SHEATH

(71) Applicant: Boston Scientific Scimed, Inc., Maple Grove, MN (US)

(72) Inventors: Thomas Clancy, Alpharetta, GA (US); Mark Hera, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 95 days.

This patent is subject to a terminal disclaimer.

(21) Appl. No.: 16/179,235

(22) Filed: Nov. 2, 2018

(65) Prior Publication Data
US 2019/0069926 A1 Mar. 7, 2019

Related U.S. Application Data

(63) Continuation of application No. 14/872,554, filed on Oct. 1, 2015, now Pat. No. 10,143,491.

(60) Provisional application No. 62/058,949, filed on Oct. 2, 2014.

(51) Int. Cl.
*A61B 17/34* (2006.01)
*A61B 1/307* (2006.01)
*A61B 1/00* (2006.01)
*A61B 17/00* (2006.01)

(52) U.S. Cl.
CPC ...... *A61B 17/3423* (2013.01); *A61B 1/00154* (2013.01); *A61B 1/307* (2013.01); *A61B 1/0011* (2013.01); *A61B 17/3439* (2013.01); *A61B 2017/00867* (2013.01); *A61B 2017/345* (2013.01)

(58) Field of Classification Search
CPC ..................... A61B 2017/345; A61B 17/3423
See application file for complete search history.

(56) References Cited

U.S. PATENT DOCUMENTS

2011/0282353 A1  11/2011  McHugo
2015/0238178 A1  8/2015  Carroux

*Primary Examiner* — Andrew Yang
(74) *Attorney, Agent, or Firm* — Bookoff McAndrews, PLLC (57) ABSTRACT

Expandable access sheaths and methods for use thereof are disclosed. The access sheath may have an expandable element and flexible membrane. The access sheath may be configured to move between a non-expanded configuration and an expanded configuration. The access sheath may be biased towards the non-expanded configuration.

20 Claims, 4 Drawing Sheets

FIG. 4

EXPANDABLE ACCESS SHEATH

CROSS-REFERENCE TO RELATED APPLICATIONS

This application is a continuation of U.S. application Ser. No. 14/872,554, filed Oct. 1, 2015, which claims the benefits of priority from U.S. Provisional Application No. 62/058,949, filed Oct. 2, 2014, the entirety of each of which is incorporated herein by reference.

TECHNICAL FIELD

The present disclosure pertains to medical devices, and methods for manufacturing medical devices. More particularly, the present disclosure pertains to a dilator having an expandable sheath.

BACKGROUND

Ureteroscopy is a procedure that can be used when urethral, ureteral, or kidney stones, strictures, or tumors are present. Ureteral stones are generally formed in the kidney and pass down into the ureter where they become lodged. In the ureter, stones block the passage of urine to the bladder, generating pain for a patient. Often, infection ensues, and in certain cases the infection can be life threatening. Ureteroscopy enables a surgeon to access, disintegrate, and remove ureteral stones.

Strictures are a constriction of the ureter associated with abnormal tissue. A stricture can result for various reasons, including congenital abnormalities, previous surgery, passage of stones, or radiation therapy. Ureteroscopy allows a surgeon to locate and repair a stricture using tools, such as expandable balloons and lasers.

Ureteroscopy also can be used when tumors are present in the kidney or ureter. Using ureteroscopy, surgeons can better diagnose the cancer by taking tissue samples. In some cases, the cancer can be treated through the use of an ureteroscopy procedure, thereby avoiding the use of more invasive techniques. Accordingly, devices and related methods are needed to allow a medical professional to undertake such procedures.

BRIEF SUMMARY

The disclosure is directed to several alternative designs, materials and methods of manufacturing medical device structures and assemblies.

In a first example, a dilator access sheath may include an access sheath having a proximal end, a distal end, and a lumen extending between the proximal end and the distal end, the access sheath having an expandable element and a flexible membrane and wherein the access sheath may be designed to move between a non-expanded configuration and an expanded configuration, a hub may be coupled to the proximal end of the access sheath, and the access sheath is biased towards the non-expanded configuration.

Alternatively or additionally to any of the examples above, in another example, the access sheath may be configured to move to the expanded configuration when a device is disposed within the lumen of the access sheath.

Alternatively or additionally to any of the examples above, in another example, an inner diameter of the access sheath in the expanded configuration may be similar in size to an outer diameter of the device disposed within the lumen of the access sheath.

Alternatively or additionally to any of the examples above, in another example, an inner diameter of the access sheath in the non-expanded configuration may be smaller than an outer diameter of the device disposed within the lumen of the access sheath.

Alternatively or additionally to any of the examples above, in another example, the expandable element may include a plurality of woven filaments.

Alternatively or additionally to any of the examples above, in another example, the expandable element may include a plurality of braided filaments.

Alternatively or additionally to any of the examples above, in another example, an angle of the filaments at their crossing points in the expanded configuration may be greater than an angle of the filaments at the crossing points in the non-expanded configuration.

Alternatively or additionally to any of the examples above, in another example, the expandable element may include one or more helically wound filaments.

Alternatively or additionally to any of the examples above, in another example, a pitch of the one or more helically wound filaments in the expanded configuration may be less than a pitch of the one or more helically wound filaments in the non-expanded configuration.

Alternatively or additionally to any of the examples above, in another example, the expandable element may include nitinol.

Alternatively or additionally to any of the examples above, in another example, the access sheath may further include a hydrophilic coating on an inner surface thereof and a hydrophilic coating on an outer surface thereof. Such coating may be applied to the flexible membrane, the expandable element, or both Alternatively or additionally to any of the examples above, in another example, the flexible membrane may be coextruded with the expandable element.

Alternatively or additionally to any of the examples above, in another example, the access sheath may further include a dilator having a proximal end and a distal end, the dilator disposed within the lumen of the access sheath and configured to be removable therefrom.

Alternatively or additionally to any of the examples above, in another example, the access sheath may further include a second hub affixed to the proximal end of the dilator.

Alternatively or additionally to any of the examples above, in another example, an inner diameter of the access sheath in the expanded configuration may be similar in size to an outer diameter of the dilator disposed within the lumen of the access sheath.

Alternatively or additionally to any of the examples above, in another example, a dilator access sheath may include a flexible sheath having a proximal end, a distal end, and a lumen extending between the proximal end and the distal end, the flexible sheath having an expandable element and a flexible membrane and wherein the flexible sheath may be designed to move between a non-expanded configuration and an expanded configuration, a hub may be coupled to the proximal end of the flexible sheath, and the flexible sheath is biased towards the non-expanded configuration.

Alternatively or additionally to any of the examples above, in another example, the flexible sheath may be configured to move to the expanded configuration when a device is disposed within the lumen of the flexible sheath.

Alternatively or additionally to any of the examples above, in another example, an inner diameter of the flexible sheath in the expanded configuration may be similar in size to an outer diameter of the device disposed within the lumen of the flexible sheath.

Alternatively or additionally to any of the examples above, in another example, an inner diameter of the flexible sheath in the non-expanded configuration may be smaller than an outer diameter of the device disposed within the lumen of the flexible sheath.

Alternatively or additionally to any of the examples above, in another example, the expandable element may include a plurality of woven filaments.

Alternatively or additionally to any of the examples above, in another example, an angle of the filaments at their crossing points in the expanded configuration may be greater than an angle of the filaments at the crossing points in the non-expanded configuration.

Alternatively or additionally to any of the examples above, in another example, the expandable element may include a plurality of braided filaments.

Alternatively or additionally to any of the examples above, in another example, an angle of the filaments at their crossing points in the expanded configuration may be greater than an angle of the filaments at the crossing points in the non-expanded configuration.

Alternatively or additionally to any of the examples above, in another example, the expandable element may include one or more helically wound filaments.

Alternatively or additionally to any of the examples above, in another example, a pitch of the one or more helically wound filaments in the expanded configuration may be less than a pitch of the one or more helically wound filaments in the non-expanded configuration.

Alternatively or additionally to any of the examples above, in another example, the expandable element may include nitinol.

Alternatively or additionally to any of the examples above, in another example, a dilator access sheath assembly may include an access sheath having a proximal end, a distal end, and a lumen extending between the proximal end and the distal end, the access sheath having an expandable element and a flexible membrane and the access sheath configured to move between a non-expanded configuration and an expanded configuration, a dilator having a proximal end and a distal end, the dilator disposed within the lumen of the access sheath and configured to be removable therefrom, a first hub affixed to the proximal end of the dilator, and a second hub affixed to the proximal end of the access sheath, and wherein the access sheath is biased towards the non-expanded configuration.

Alternatively or additionally to any of the examples above, in another example, an inner diameter of the access sheath in the expanded configuration may be similar in size to an outer diameter of a device disposed within the lumen of the flexible sheath.

Alternatively or additionally to any of the examples above, in another example, the expandable element may include a plurality of woven or braided filaments.

Alternatively or additionally to any of the examples above, in another example, an angle of the filaments at their crossing points in the expanded configuration may be greater than an angle of the filaments at the crossing points in the non-expanded configuration.

Alternatively or additionally to any of the examples above, in another example, the expandable element may include nitinol.

Alternatively or additionally to any of the examples above, in another example, a method may include inserting a dilator and access sheath assembly into a body lumen, the access sheath having a non-expanded configuration and an expanded configuration, advancing the dilator and access sheath assembly to a required destination, removing the dilator from the body lumen, and advancing a device through a lumen of the access sheath, wherein the dilator dilates the body lumen to a first diameter and advancing the device through the lumen of the access sheath moves the access sheath to the expanded configuration and dilates the body lumen to a second diameter larger than the first diameter.

Alternatively or additionally to any of the examples above, in another example, the method may further include removing the device from the lumen of the access sheath.

Alternatively or additionally to any of the examples above, in another example, upon removal of the device from the lumen of the access sheath, the access sheath may move to the non-expanded configuration.

Alternatively or additionally to any of the examples above, in another example, the access sheath may be biased towards the non-expanded configuration.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The present disclosure relates to a dilator having a flexible sheath having an expandable element and a flexible membrane. The dilator can be used with an access sheath in various surgical procedures requiring access, through, for example, a vessel in the body. Ureteroscopy procedures are a non-limiting example of such procedures. Other procedures include an endopyelotomy procedure to treat an uretero-pelvic junction obstruction, the treatment of urethral or ureteral strictures, percutaneous renal surgery, and vascular access surgery.

In an ureteroscopy procedure, a guide wire is introduced into the urethra. The wire then is fed through the urinary tract into the bladder. From the bladder, the wire passes through the ureteral orifice and into the ureter. If access to the kidney is required, the wire is fed through the ureter, to the kidney, where its distal end can be lodged.

In some ureteroscopy procedures, after introducing the guide wire, a medical professional may have several choices. For example, the medical professional can introduce a dilating element that is connected to a surrounding sheath over the guide wire. As the dilating element is introduced over the guide wire, the dilating element radially expands the tissue of the urinary tract. After the dilator with the connected surrounding sheath has been guided to its required destination, the dilating element may be detached from the sheath and removed from the lumen of the sheath, leaving the sheath in place. In another example, after the guide wire is introduced, a medical professional can slide a sheath that also functions as a dilating element over the length of the guide wire. This type of device may generally have a tapered tip to gradually dilate tissue.

Devices used in flexible ureteroscopy may continue to be miniaturized and modified in the pursuit of reducing trauma during procedures. Access sheaths may be widely used in flexible ureteroscopy but their miniaturization may be limited. Some sheaths that are currently used may dilate the ureter to sizes that are much larger than its natural diameter. They may dilate the ureter axially which may create shear forces that can damage the ureteral orifice and cause tears in the ureteral wall. However, making an access sheath smaller would require the miniaturization of every device that is designed to pass through a sheath. An expandable access sheath may allow the access sheath to be smaller without having to redesign an entire line of ureteroscopic devices. It may also reduce trauma by dilating the ureter to a smaller size in a way that minimizes shear forces.

Figure 1:
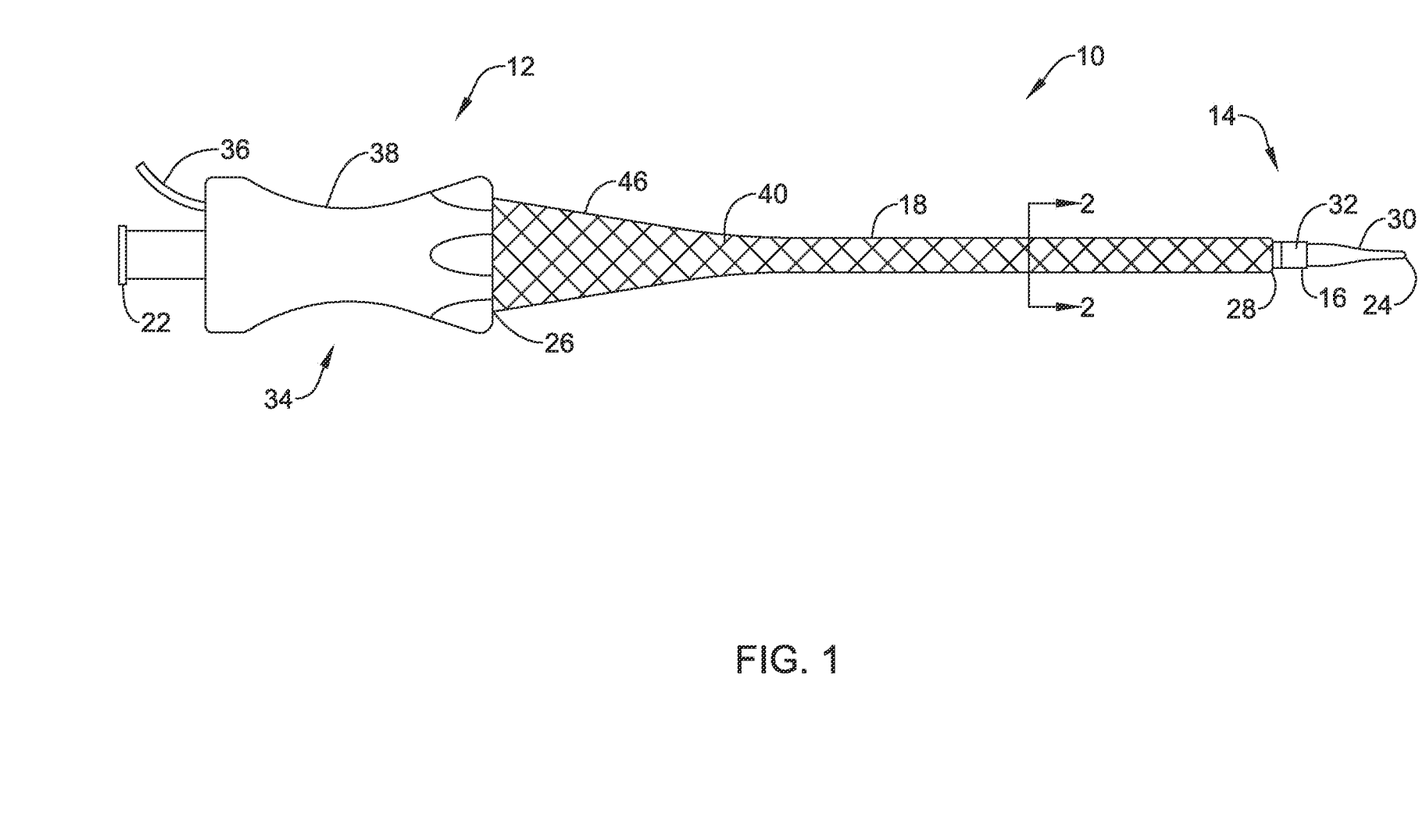
FIG. 1 is side view of an illustrative dilator access sheath assembly.

FIG. 1 is a side view of an illustrative dilator access sheath assembly 10 having a proximal end region 12 and a distal end region 14. The assembly 10 may include a dilator 16 and a flexible expandable access sheath 18. In some embodiments, the dilator 16 may include a lumen 20 (shown in FIG. 2) extending from a proximal end 22 to a distal end 24 of the dilator 16 for advancing the dilator 16 over a guidewire. Alternatively, the dilator 16 may be solid and utilized without a guidewire. The dilator 16 may be sufficiently rigid along its length to perform its dilation function. This may allow the dilator 16 to dilate tissue without buckling. For example, the dilator 16 can be made from a material having a durometer value of about 40 to about 80 on a Shore A scale, about 45 to about 75 on a Shore A scale, about 50 to about 70 on a Shore A scale, or about 55 to about 65 on a Shore A scale. These durometers are sufficiently hard so that the dilator 16 may be sufficiently rigid to dilate tissue in a body vessel. The thickness of the wall of the dilator 16 also can be varied to create sufficient rigidity, and/or reinforcing materials can be used. The dilator 16 can be manufactured using an extrusion process and can be made from, for example, but without limitation, polyethylene, such as polyethylene having a molecular weight in the range of 50,000 to 100,000; nylon, such as nylon 12, nylon 4-6, and nylon 6-6; Pebax (polyether block amides), for example having a durometer value of about 60 to about 85 on a Shore D scale; polyurethane, for example having a durometer value of about 75 on a Shore D scale; polytetrafluoroethylene (PTFE), particularly fluorinated ethylene propylene (FEP) copolymers; and polyethylene impregnated with PTFE. In certain embodiments, the dilator is made from materials with a flex modulus of about 300 to about 500 MPa.

The external surface of the dilator 16 can have a hydrophilic coating or a silicone coating to ease the passage of the dilator in tissue, although this is not required. Such a hydrophilic coating can be, for example, but without limitation, N-Vinyl Pyrrolidone, Poly Vinyl Alcohol, and Poly Vinyl Pyrrolidone. The hydrophilic coating can be accomplished by coating a device with a primer, such as Bayhydrol 110 (an anionic dispersion of an aliphatic polyester urethane resin in water/n-methyl-2pyrrolidone) and then bonding a primary layer over the primer. The primary layer can be, without limitation, an acrylamide or a polyurethane-based acrylamide. Alliphatic polyether and polyester polyurethanes can also be used as lubricous coatings.

In some embodiments, the distal end 24 of the dilator 16 may have a tapered tip 30. The tapered tip 30 may be formed as a unitary structure with the dilator 16. Alternatively, the tapered tip 30 can be a separate part that is designed to mate with the dilator 16 using any technique known in the art, such as, but without limitation, a press fit, a snap fit, threading, or welding. The dilator 16 may further include a radiopaque marker 32 positioned adjacent to the distal end 24 thereof to facilitate advancement and/or placement of the dilator 16.

The assembly 10 may further include a hub assembly 34 positioned adjacent to the proximal end region 12 thereof. The hub assembly 34 may include a first hub 36 affixed to the dilator 16 adjacent to the proximal end 22 thereof and a second hub 38 affixed to the expandable access sheath 18 adjacent to the proximal end 26 thereof. In some instances, the first hub 36 may be a bi-furcated hub, although this is not required. In use, the first hub 36 may be received within the second hub 38. In some embodiments, the first and second hubs 36, 38 can connect through the use of a friction fit, snap-fit or a compression fit, or by locking, or twisting. During use, the second hub 38 holds the first hub 36 securely in place, such that movement of the dilator 16 relative to the access sheath 18 is minimal or non-existent. Once use of the dilator 16 is no longer required, the dilator 16 can be disconnected and removed from the access sheath 18, leaving the access sheath 18 in place.

The access sheath may include a lumen 44 (shown in FIG. 2) extending from a proximal end 26 to a distal end 28 of the access sheath 18. When the dilator access sheath assembly 10 is assembled, the expandable access sheath 18 may be coaxially disposed over and surrounding the dilator 16. For example, the dilator 16 may be disposed within the lumen 44 of the access sheath 18. When the access sheath 18 and the dilator 16 are in use, the distal end 28 of the access sheath 18 may be spaced a distance from the distal end 24 of the dilator 16. Alternatively, the distal end 28 of the access sheath 18 can partially or fully cover the distal end 24 of the dilator 16. While the expandable access sheath 18 and dilator 16 are illustrated as having a circular cross-section, it is contemplated that the expandable access sheath 18 and dilator 16 may have other cross-sectional shapes, as desired. For example, the access sheath 18 and/or dilator 16 can have an oval cross section. The access sheath 18 has a proximal end 26 and a distal end 28 defining a length therebetween. In some instances, the access sheath 18 may include a tapered region 46 such that the proximal end 26 has a larger cross-section than the distal end 28. This may ease the initial insertion of a device, such as, but not limited to an ureteroscope, into the expandable access sheath 18.

Generally, the expandable access sheath 18 may be less rigid than dilator 16, but sufficiently rigid to avoid buckling, and may be formed using an extrusion process. For example, the access sheath 18 can be made from a material having a durometer value of about 30 to about 50 on a Shore A scale or about 35 to about 45 on a Shore A scale. The wall of the access sheath 18 can also be varied in thickness to vary rigidity, and/or reinforcing materials can be used. To reduce friction when the access sheath 18 is introduced into the body, the access sheath 18 can have a hydrophilic coating, such as those described above. Additionally, the access sheath 18 can be coated or be formed integrally with one or more agents to provide, for example, an anti-inflammatory, analgesic, anti-spasmodic, or anti-microbial effect, alone or in combination, when inserting or upon insertion of the access sheath. Other types of agents are contemplated within the scope of disclosure for use as a coating on the access sheath or within the access sheath to provide a therapeutic or healing effect. For example, but without limitation, Toradol (ketorolac tromethamine), or Ditropan (oxybutynin chloride), may be incorporated on or into the access sheath to aid healing of urinary tract tissue or to relieve discomfort.

The expandable access sheath 18 can be manufactured from one layer of material or from multiple overlaid or fused layers of the same or different materials, and may or may not include a reinforcing member to increase column strength. For example, an inner surface of the access sheath 18 can include, for example, PTFE, or, as another example, Pebax. The reinforcing member can be a stainless steel coil, and the outer surface can include, for example, Pebax, or, as another example, Hytrel (a polyether ester elastomer block copolymer consisting of a hard crystalline segment of polybutylene terephthalate and soft amorphous segments based on long-chain polyether glycols). In some cases, a tie layer exists between the inner PTFE surface and the outer Pebax or Hytrel surface. When Pebax is used as an inner or outer surface, Pebax having a durometer value of about 45 to about 72 on a shore D scale can be used. The access sheath 18 also can be made from polyurethanes having a durometer value of about 45 to about 72 on a shore D scale, nylons, or PTFE impregnated with either Pebax or nylons.

Figure 2:
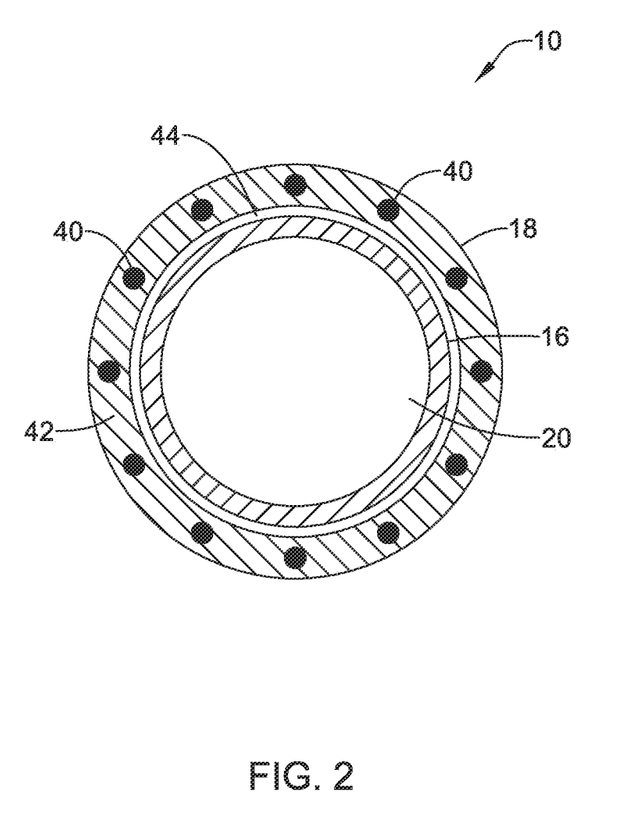
FIG. 2 is a cross-section of the dilator access sheath assembly of FIG. 1 taken along line 2-2 of FIG. 1.

Referring additionally to FIG. 2, which illustrates a cross-section of the dilator access sheath assembly 10 taken along line 2-2 of FIG. 1, the expandable access sheath 18 may include an expandable element 40 disposed within a flexible membrane 42. It is contemplated that the expandable element 40 may be formed from a single filament or multiple filaments as desired. For example, one, two, three, four, or more filaments may be braided, woven, or otherwise intertwined to form an expandable network. It is further contemplated that one or more filaments may be helically wound to form an expandable coil or spring-like structure (see, for example, FIG. 4). In some embodiments, the flexible membrane 42 may be a single layer with the expandable element 40 embedded therein. In some embodiments, the flexible membrane 42 may be coextruded with the expandable element 40 to embed the expandable element within the flexible member 42. In other instances, the expandable element 40 may be disposed between two or more layers of like or different materials. In other embodiments, the flexible membrane 42 may be applied by coating the expandable element 40. For example, the flexible membrane 42 may be coated over the flexible membrane in its braided, woven, or coiled configuration. Alternatively, the flexible membrane 42 may be formed over individual filaments prior to forming the expandable element 40 into its delivery configuration. The flexible membrane 42 may further include a hydrophilic coating on the inner and/or outer surfaces thereof to enhance lubricity. The flexible membrane 42 may be selected to conform to its surroundings while also protecting the body lumen from the devices being advanced through the lumen 44 of the access sheath 18. In some embodiments, the flexible membrane 42 may be elastomeric. In some instances, the flexible membrane may be clear or opaque to allow for visual inspection of the ureter even while the access sheath 18 is in place.

The expandable access sheath 18 may be configured to move between a smaller, non-expanded or collapsed configuration and a larger, expanded configuration. In some instances, the expandable access sheath 18 may be biased towards the non-expanded configuration. It is contemplated that the size of the expanded configuration may be determined by the size of the device being advanced through the access sheath 18. For example, the access sheath 18 may generally take on the size of the device being advanced through it. The smaller diameter of the non-expanded access sheath 18 may reduce shear force trauma as it is pushed up the ureter. Once the access sheath 18 is in place, the ureteroscope, or other device, may expand the access sheath 18 to further dilate the ureter as it is advanced through the sheath 18. With the access sheath 18 fully expanded, its outside diameter may be smaller than traditional access sheaths. As the ureteroscope is removed, the access sheath 18 may contract back to its original (non-expanded) size. This may minimize shear forces when the access sheath 18 is pulled out of the ureter. It may also prevent the access sheath 18 from getting stuck on any strictures that it may have expanded around during the procedure. It is further contemplated that the expandable access sheath 18 may allow the ureter, or other body lumen, to be dilated in a two-step procedure. First, the dilator access sheath assembly 10, with dilator 16, may dilate the ureter to a first diameter. Then a device advanced through the access sheath 18 may further dilate the ureter to a second, larger diameter. Two-step dilation may allow the ureter to expand radially, the direction in which it is naturally designed to dilate, in a more gradual manner. Dilating the ureter to a smaller size using this process may minimize shear forces and prevent or reduce trauma during flexible ureteroscopy.

The expandable element 40 may be configured allow the access sheath 18 to expand and contract as devices are introduced or withdrawn. In some embodiments, the expandable element 40 may be formed from a shape memory material, such as, but not limited to nitinol. For example, the expandable element 40 may be formed such that the "remembered" state of expandable element 40 is the smaller, contracted shape. An external force, such a device being inserted through the lumen 44 of the access sheath 18 may cause the expandable element and flexible membrane 42 to expand into a larger, expanded shape. For example, as a device is inserted through the lumen 44 of the access sheath 18 (after the dilator 16 has been removed), the force of the device may be sufficient to cause the expandable element 40 and flexible membrane 42 to expand as the device is passed through. Once the device is withdrawn, the expandable element 40 may assume its "remembered" contracted state.

In other embodiments, the structure of the expandable element 40 may allow the access sheath 18 to expand and contract without the use of shape memory materials. For example, the force of a device on a braided or woven expandable element 40 may increase the angle A2 of the filaments at their crossing points 60b along a longitudinal axis of the access sheath thus increasing the diameter of the access sheath 18 while reducing the length of the access sheath 18. As the device is removed, the angle A1 of the filaments along a longitudinal axis of the access sheath may be reduced at their crossing points 60a thus decreasing the diameter of the access sheath 18 while increasing the length of the access sheath 18 (see, for example, FIG. 3). In some instances, the braided or woven expandable element may not be secured at the crossing points 60a, 60b to allow for movement of the filaments relative to one another. It is contemplated that a helically wound coil may also be used to allow the access sheath 18 to expand and contract. For example, the force of a device on a helically wound expandable element 40 may reduce the pitch (e.g. distance between adjacent windings) of the filament(s) thus increasing the diameter of the access sheath 18 while reducing the length of the access sheath 18. As the device is removed, the pitch of the filament(s) may be increased decreasing the diameter of the access sheath 18 while increasing the length of the access sheath 18.

Figure 3:
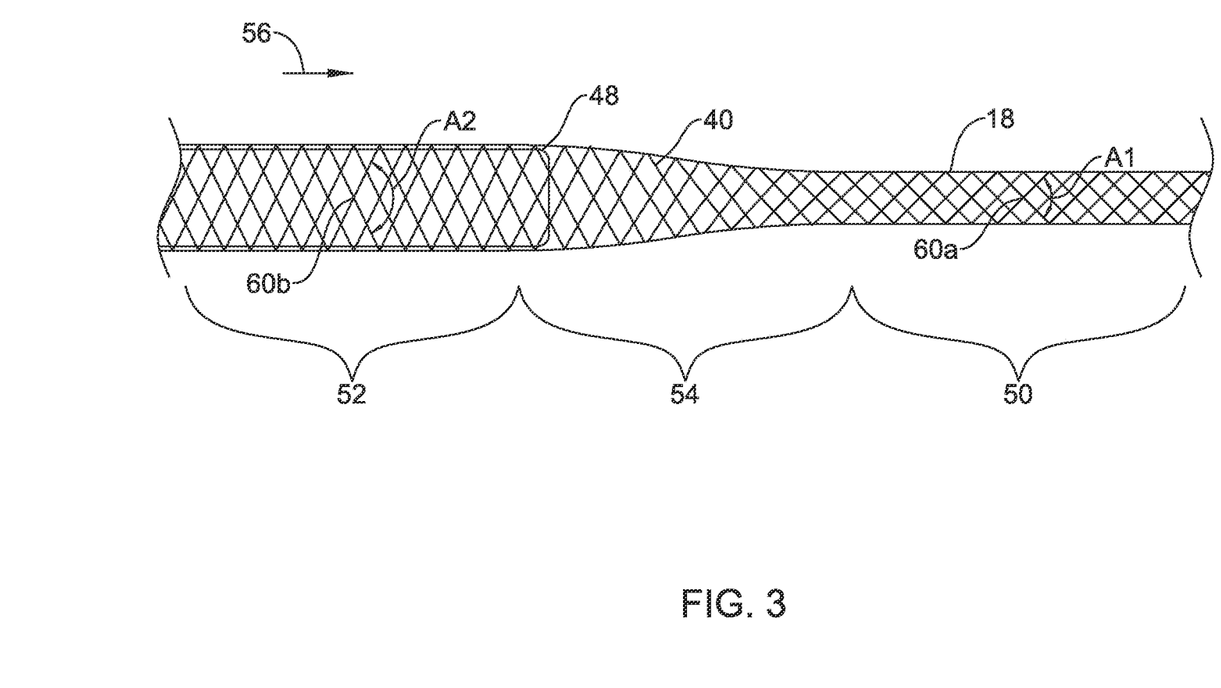
FIG. 3 is a schematic side view of a scope passing through an expandable access sheath.

Now referring additionally to FIG. 3, in an ureteroscopy procedure according to the disclosure, the patient can be given local or general anesthetic. A guide wire may then be introduced into the urethra and is fed through the bladder, ureteral orifice, and ureter to the kidney (not explicitly shown). The proximal end of the guide wire then is introduced into the distal end region 14 of the dilator access sheath assembly 10 such that the dilator access sheath assembly slides over the guide wire (not explicitly shown). The distal end 24 of the dilator 16 is advanced to the orifice of the urethra. As the distal end 24 of the dilator 16 moves along the urethra, it applies radial pressure to the tissue of the urinary tract, gradually dilating such tissue to a first diameter. Gradual dilation may reduce trauma to the patient. The tapered tip 30 of the dilator 16 facilitates, in part, such gradual dilation. Dilating the urinary tract allows the access sheath 18 of the dilator access sheath assembly 10 to be inserted into the body (not explicitly shown).

The dilator access sheath assembly 10 may then be further guided to its required destination. Once the dilator access sheath assembly 10 is located at the desired location, the dilator 16 may be disconnected from the access sheath 18 and removed from the lumen 44 of the access sheath 18, thereby allowing other tools to be inserted into the lumen. An ureteroscope, or other tool, 48 may be advanced through the lumen 44 of the access sheath 18. As the ureteroscope 48 is distally advanced in the direction of arrow 56, the expandable element 40 may expand from a non-expanded configuration to an expanded configuration and thus expanding the body lumen to a second diameter larger than the first diameter. As shown in FIG. 3, a distal region 50, absent the ureteroscope may retain the non-expanded configuration until the ureteroscope is advanced to the region. For example, the access sheath 18 is only expanded in regions 52 where the ureteroscope is disposed. In the expanded configuration, the access sheath 18 may assume an inner diameter or profile similar to the outer diameter of the device being advanced therethough. In some instances, a tapered or partially expanded region 54 may be present between expanded region 52 and the non-expanded region 50. As the ureteroscope is proximally retracted, the access sheath 18 may assume its non-expanded configuration without user intervention. It is contemplated that the expandable access sheath 18 remains contracted at all times unless a device, such as ureteroscope 48 is inside of the access sheath 18. The contraction of the access sheath 18 after a device is removed may greatly reduce trauma. For example, if the access sheath 18 was expanded around a stricture during the procedure and it was unable to contract, the access sheath 18 may get stuck in the ureter and would have to be removed surgically. Just as the access sheath's small diameter may reduce shear forces during insertion, it may also do so upon removal of the access sheath 18 as well. It is contemplated that with an ureteroscope 48 in place and the expandable access sheath 18 fully expanded, the expandable access sheath may have an outside diameter that is smaller than other access sheaths.

Figure 4:
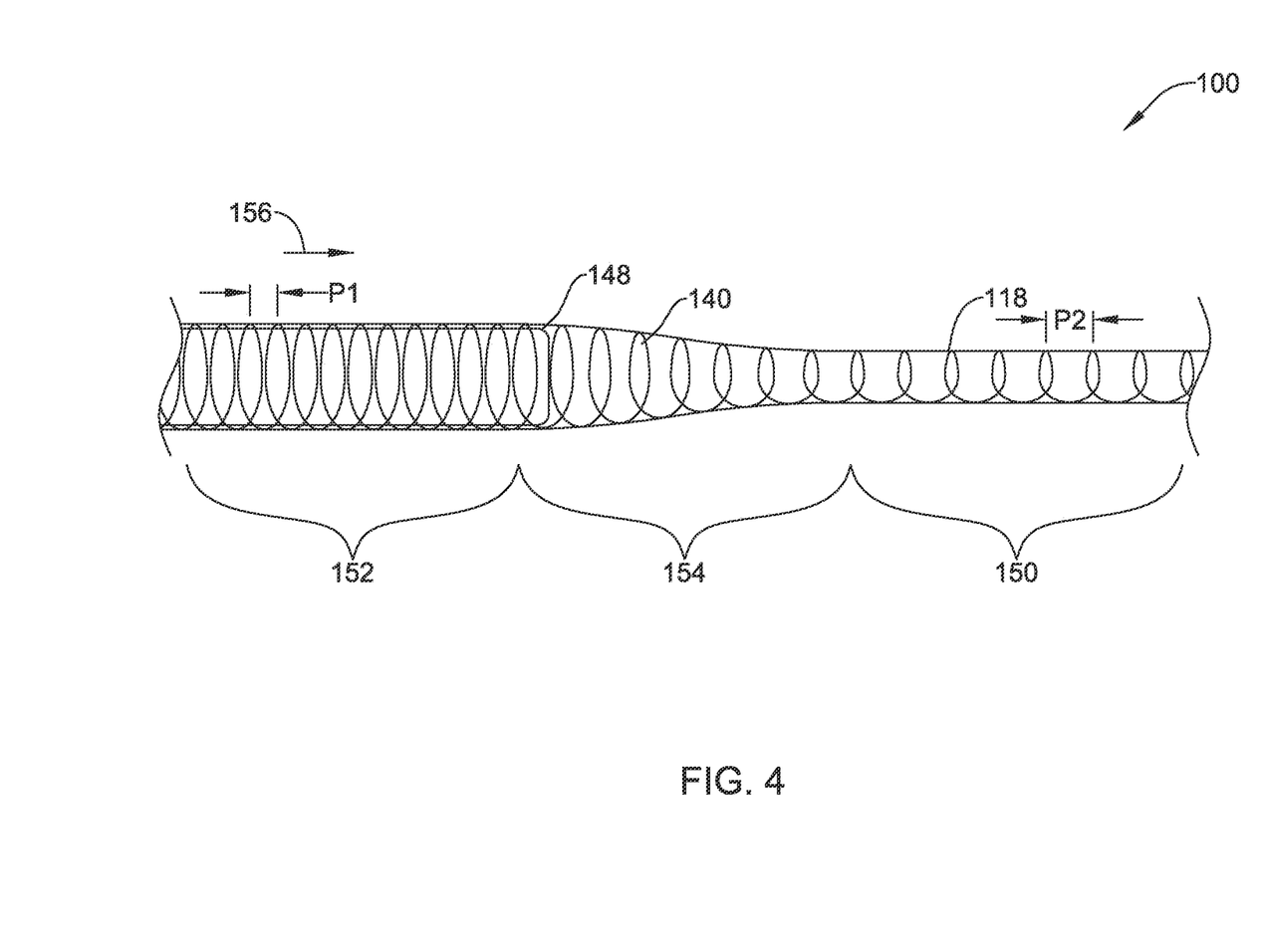
FIG. 4 is a schematic side view of a scope passing through another illustrative expandable access sheath.

FIG. 4 illustrates a portion of an ureteroscopy procedure using an alternative dilator access sheath assembly 100. The dilator sheath assembly 100 may be similar in form and function to dilator access sheath assembly 100. Now referring additionally to FIG. 4, in an ureteroscopy procedure according to the disclosure, the patient can be given local or general anesthetic. A guide wire may then be introduced into the urethra and is fed through the bladder, ureteral orifice, and ureter to the kidney (not explicitly shown). The proximal end of the guide wire then is introduced into the distal end region of the dilator access sheath assembly 100 such that the dilator access sheath assembly 100 slides over the guide wire (not explicitly shown). The distal end of the dilator is advanced to the orifice of the urethra. As the distal end of the dilator moves along the urethra, it applies radial pressure to the tissue of the urinary tract, gradually dilating such tissue to a first diameter. Gradual dilation may reduce trauma to the patient. The tapered tip of the dilator facilitates, in part, such gradual dilation. Dilating the urinary tract allows the access sheath 118 of the dilator access sheath assembly 100 to be inserted into the body (not explicitly shown).

The dilator access sheath assembly 100 may then be further guided to its required destination. Once the dilator access sheath assembly 100 is located at the desired location, the dilator may be disconnected from the access sheath 118 and removed from the lumen of the access sheath 118, thereby allowing other tools to be inserted into the lumen. An ureteroscope, or other tool, 148 may be advanced through the lumen of the access sheath 118. As the ureteroscope 148 is distally advanced in the direction of arrow 156, the expandable element 140 may expand from a non-expanded configuration to an expanded configuration and thus expanding the body lumen to a second diameter larger than the first diameter. As shown in FIG. 4, a distal region 150, absent the ureteroscope, may retain the non-expanded configuration until the ureteroscope 148 is advanced to the region. For example, the access sheath 118 is only expanded in regions 152 where the ureteroscope 148 is disposed. It is contemplated that a helically wound coil 140 may also be used to allow the access sheath 118 to expand and contract. For example, the force of a device on a helically wound expandable element 140 may reduce the pitch (e.g. distance between adjacent windings) of the filament(s) thus increasing the diameter of the access sheath 18 while reducing the length of the access sheath 18. For example, the pitch P1 of the expanded region 152 may be less than the pitch P2 of the non-expanded region 150. As the device 148 is removed, the pitch of the filament(s) may be increased thus decreasing the diameter of the access sheath 118 while increasing the length of the access sheath 118.

In the expanded configuration, the access sheath 118 may assume an inner diameter or profile similar to the outer diameter of the device 148 being advanced therethough. In some instances, a tapered or partially expanded region 154 may be present between expanded region 152 and the non-expanded region 150. As the ureteroscope is proximally retracted, the access sheath 118 may assume its non-expanded configuration without user intervention. It is contemplated that the expandable access sheath 118 remains contracted at all times unless a device, such as ureteroscope 148 is inside of the access sheath 118. The contraction of the access sheath 118 after a device is removed may greatly reduce trauma. For example, if the access sheath 118 was expanded around a stricture during the procedure and it was unable to contract, the access sheath 118 may get stuck in the ureter and would have to be removed surgically. Just as the access sheath's small diameter may reduce shear forces during insertion, it may also do so upon removal of the access sheath 118 as well. It is contemplated that with an ureteroscope 148 in place and the expandable access sheath 118 fully expanded, the expandable access sheath may have an outside diameter that is smaller than other access sheaths.

Assemblies 10, 100, and the various components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. In some other embodiments, a superelastic alloy, for example a superelastic nitinol can be used to achieve desired properties.

In at least some embodiments, portions or all of assemblies 10, 100 may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of assemblies 10, 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of assemblies 10, 100 to achieve the same result.

In some embodiments, a degree of Magnetic Resonance Imaging (MRI) compatibility is imparted into assemblies 10, 100. For example, assembly 10 or portions thereof, may be made of a material that does not substantially distort the image and create substantial artifacts (i.e., gaps in the image). Certain ferromagnetic materials, for example, may not be suitable because they may create artifacts in an MRI image. Assemblies 10, 100 or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers for assemblies 10, 100 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A dilator access sheath, comprising:
a body extending between a proximal end and a distal end, the body having:
a lumen extending between the proximal end and the distal end;
an expandable element; and
a flexible membrane;
wherein the body is biased, absent the application of any force, towards a non-expanded configuration, and wherein the body is configured to move to an expanded configuration via insertion of a device within the lumen of the body.

2. The dilator access sheath of claim 1, wherein the expandable element includes a plurality of woven or braided filaments.

3. The dilator access sheath of claim 1, wherein the expandable element includes at least one helically wound filament.

4. The dilator access sheath of claim 3, wherein the at least one helically wound filament includes a coil extending between the proximal end and the distal end of the body.

5. The dilator access sheath of claim 3, wherein a pitch of the at least one helically wound filament in the expanded configuration is less than a pitch of the at least one helically wound filament in the non-expanded configuration.

6. The dilator access sheath of claim 1, wherein an inner diameter surface of the body in the expanded configuration contacts an outer diameter surface of the device disposed within the lumen of the body.

7. The dilator access sheath of claim 1, wherein an inner diameter of the body in the non-expanded configuration is smaller than an outer diameter of the device disposed within the lumen.

8. The dilator access sheath of claim 1, wherein the expandable element is biased toward the non-expanded configuration upon removal of an expansion force.

9. A dilator access sheath, comprising:
a body extending between a proximal end and a distal end, the body having:
a lumen extending between the proximal end and the distal end;
an expandable coil element; and
a flexible membrane, wherein the expandable coil element is embedded in the flexible membrane;
wherein the body is biased, absent the application of any force, towards a non-expanded configuration, and wherein the body is configured to move to an expanded configuration via insertion of a device within the lumen of the body.

10. The dilator access sheath of claim 9, wherein the expandable coil element is biased toward the non-expanded configuration upon removal of an expansion force due to removal of the device from the lumen of the body.

11. The dilator access sheath of claim 9, wherein an inner diameter surface of the body in the expanded configuration is configured to contact an outer diameter surface of the device disposed within the lumen of the body.

12. The dilator access sheath of claim 9, wherein a pitch of the expandable coil in the expanded configuration is less than a pitch of the expandable coil in the non-expanded configuration.

13. The dilator access sheath of claim 9, further including:
a first hub coupled to the proximal end of the body, wherein the first hub is configured to be coupled to a second hub at a proximal end of the device.

14. The dilator access sheath of claim 13, wherein the first hub is configured to be coupled to the second hub via a friction fit connection, a snap-fit connection, or a compression fit connection.

15. A dilator access sheath, comprising:
a radially expandable body extending between a proximal end and a distal end, the body having:
   a lumen extending between the proximal end and the distal end;
   at least one expandable filament; and
   a flexible membrane contacting the at least one expandable filament;
wherein the at least one expandable filament is biased toward a non-expanded configuration upon removal of an expansion force.

16. The dilator access sheath of claim 15, wherein the at least one expandable filament is helically wound.

17. The dilator access sheath of claim 16, wherein a pitch of the at least one helically wound filament in an expanded configuration is less than a pitch of the at least one helically wound filament in the non-expanded configuration.

18. The dilator access sheath of claim 15, wherein an inner diameter surface of the body in an expanded configuration is configured to contact an outer diameter surface of a device disposed within the lumen of the body.

19. The dilator access sheath of claim 15, further including:
a first hub coupled to the proximal end of the body, wherein the first hub is configured to be coupled to a second hub at a proximal end of a device via a friction fit connection, a snap-fit connection, or a compression fit connection.

20. The dilator access sheath of claim 15, wherein the at least one expandable filament is embedded within the flexible membrane.

* * * * *